US00PP17748P3

(12) United States Plant Patent
Gill

(10) Patent No.: US PP17,748 P3
(45) Date of Patent: May 22, 2007

(54) ***MALUS* 'SUMMER WONDER'**

(50) Latin Name: *Malus baccata×Malus pumila*
Varietal Denomination: Summer Wonder

(75) Inventor: Kenneth Ray Gill, Baileyton, AL (US)

(73) Assignee: Kenneth Gill, Baileyton, AL (US)

( * ) Notice: Subject to any disclaimer, the term of this patent is extended or adjusted under 35 U.S.C. 154(b) by 0 days.

(21) Appl. No.: 10/972,303

(22) Filed: Oct. 25, 2004

(65) Prior Publication Data

US 2006/0090230 P1 Apr. 27, 2006

(51) Int. Cl.
*A01H 5/00* (2006.01)

(52) U.S. Cl. ..... Plt./173

(58) Field of Classification Search ..... Plt./173
See application file for complete search history.

*Primary Examiner*—Kent Bell
*Assistant Examiner*—Annette H Para
(74) *Attorney, Agent, or Firm*—Juanita Gill; Tonya Sears; April Daniels

(57) ABSTRACT

Mr. Kenneth Gill in Baileyton, Ala. introduces a cultivated seedling selection of *Malus* 'Antoanovka' named 'Summer Wonder' which offers the landscape industry a unique disease resistant purple-leafed crabapple with stable color in southern climates (zones 7b/8a) with pinkishreddish purple flowers and desirably small fruit for the urban landscape.

8 Drawing Sheets

BACKGROUND OF INVENTION

Figure 1:
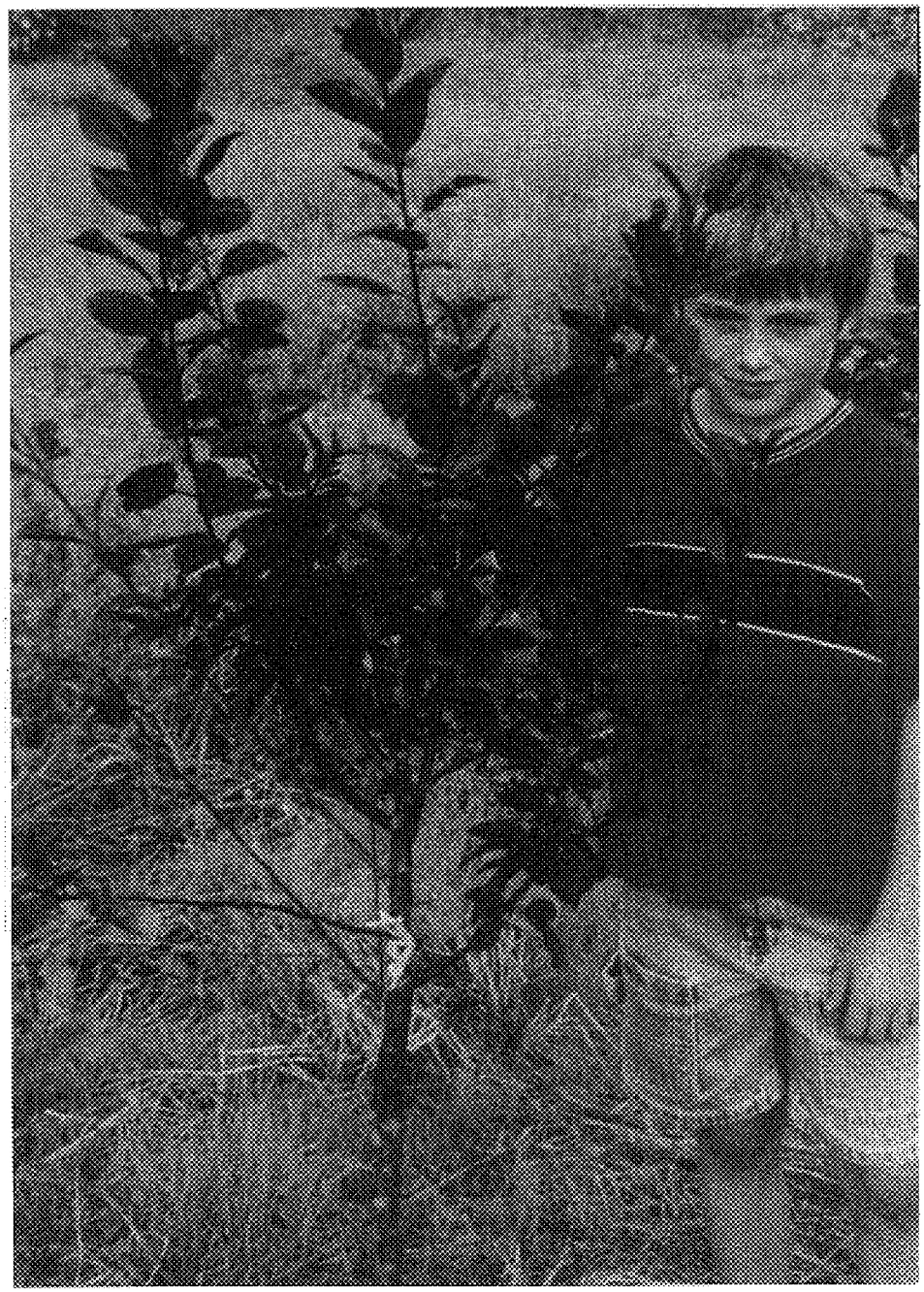

A new and distinct *Malus* tree named 'Summer Wonder' as herein described and illustrated being a genetic variation from an open pollinated seedling of the crabapple, *Malus baccata×Malus pumila* 'Antonovka', was discovered in the nursery production seedling row by the sole inventor, Mr. Kenneth Gill in Baileyton, Ala. on Jun. 5, 1998. This cultivar is of Russian origin and is used in the nursery industry as a hardy root stock for *Malus* cultivars. Seeds from this open pollinated cultivar were sown and cultivated in the field for use as budding root stock. The 'Antonovka' seed came from Quincy, Wash., 98848 collected from green leaf forms of 'Antonovka'. The new *Malus* cultivar named 'Summer Wonder' by the discoverer, Mr. Gill, has been observed and evaluated for six years as a landscape plant and has maintained its unique purple leaf characteristics. It has not been sold, shared or released and has not been made public in any publications. Summer Wonder crabapple has been successfully asexually propagated by budding in September and October on *Malus domestica* and 'Antonovka' open pollinated seedling rootstock in Cullman, Ala. at the inventor's nursery. Budding success rate has been consistent at about 80–90% success rate. The clonal progeny of the parent plant are identical to the parent and offer the same distinct characteristics. The clonal progeny of the parent plant are true to type, identical to the parent and offer the same distinct characteristics.

SUMMARY OF INVENTION

The unique characteristics expressed by this new cultivar are stable deep purple leaves which are unique to this normally green cultivar. 'Summer Wonder' has landscape desirable, very small purple fruit with reddish/purple flowers. Bottom of the leaves are also a lighter purple. The pith of the branches are also purple in color. There are other purple leaf crabapple cultivars from different *Malus* species but few, if any, that maintain the continuous purple color in the heat of climatic zones 7b/8a in Cullman, Ala. *Malus* 'Robinson' and *M.* 'Profusion' are cultivars that offer red leaves at emergence but fade to green during the summer. (See attached photo) *M.* 'Royalty' and *M.* 'Velvet Pillar' are two other cultivars noted for their purple leaves. 'Royalty' (*pumila×baccata*) is an open pollinated seedling of Rosybloom and has red fruit and is highly susceptible to fireblight and scab. 'Velvet Pillar', a patented cultivar (U.S. Plant Pat. No. 4,785) by Simpson also is noted for its purple leaves, single pink flowers and reddish fruit, listed as fair to good disease resistance. It is an upright selection 20 feet (6 m) high×14 (4.3 m) wide. 'Summer Wonder' crabapple selection has also exhibited unique resistance to typical crabapple diseases of cedar-apple rust (*Gymnosporangium juniperi-virginianae*), powdery mildew (*Podosphaera leucotricha*), apple scab (*Venturia inaequalis*) and fire blight (*Erwinia amylovora*) where clones of the tree were exposed to innoculi of the pathogens in surrounding fields of other species and cultivars of *Malus*. These diseases were evident in surrounding fields where other crabapples were moderately or severely affected. These unique and distinct characteristics separate 'Summer Wonder' from all other plants within its botanical and market class.

DESCRIPTION OF PHOTOS

Photos represent flower and fruit color, 3 year old plant in the field, fall and spring foliage and foliage of *M.* 'Summer Wonder' compared to *M.* 'Robinson' and *M.* 'Profusion' under summer heat conditions.

Figure 2:
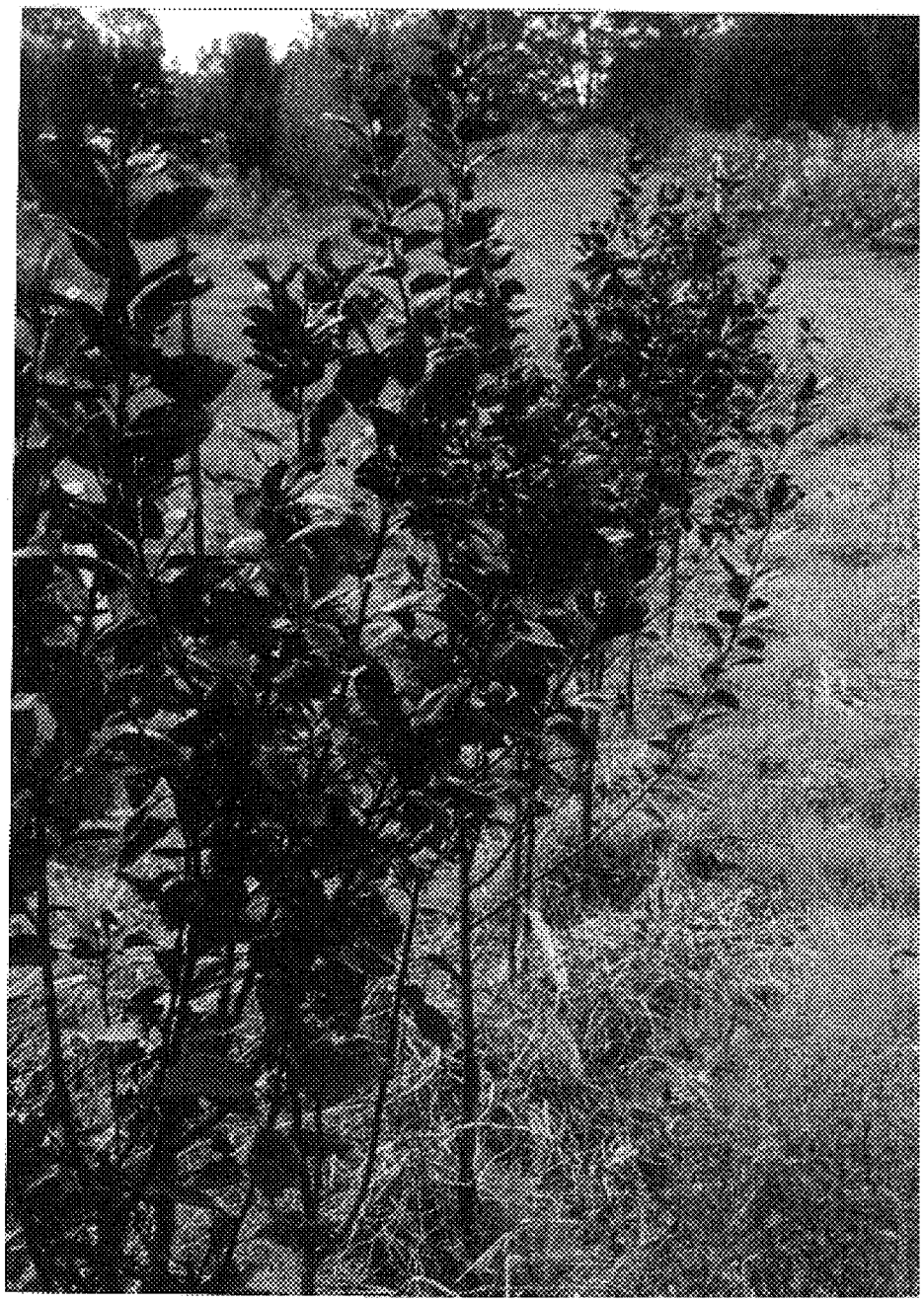
Figure 3:
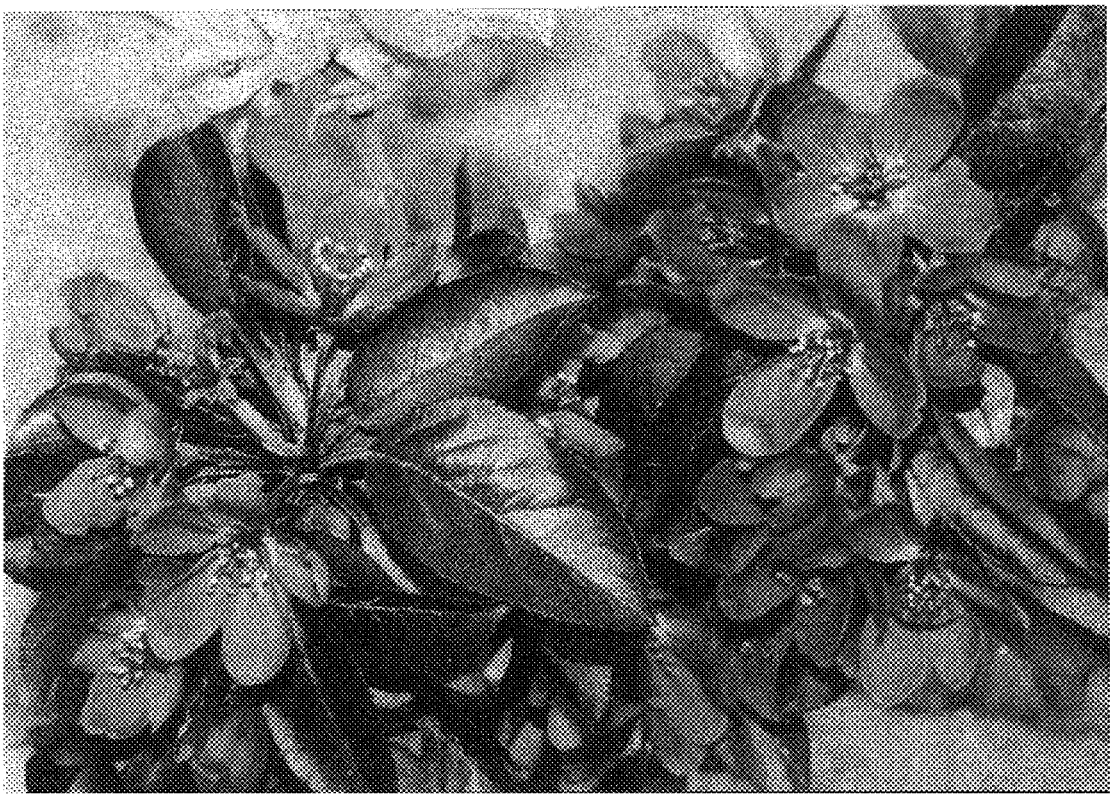
Figure 4:
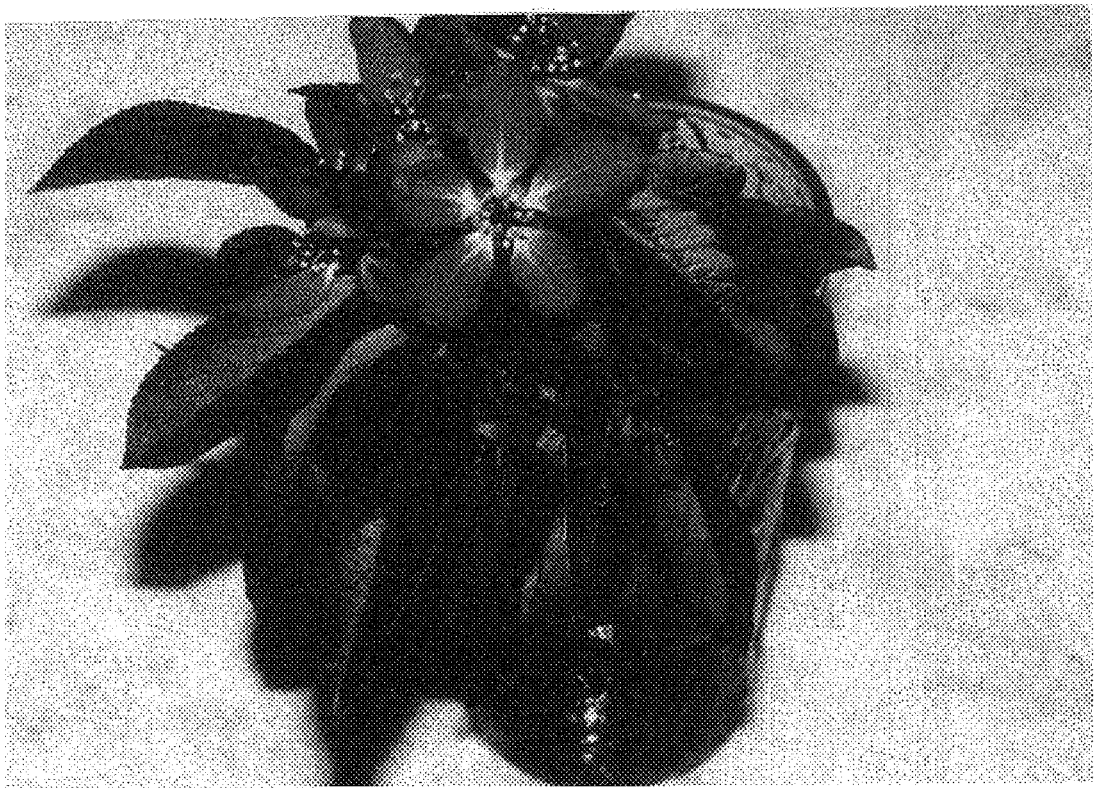
Figure 5:
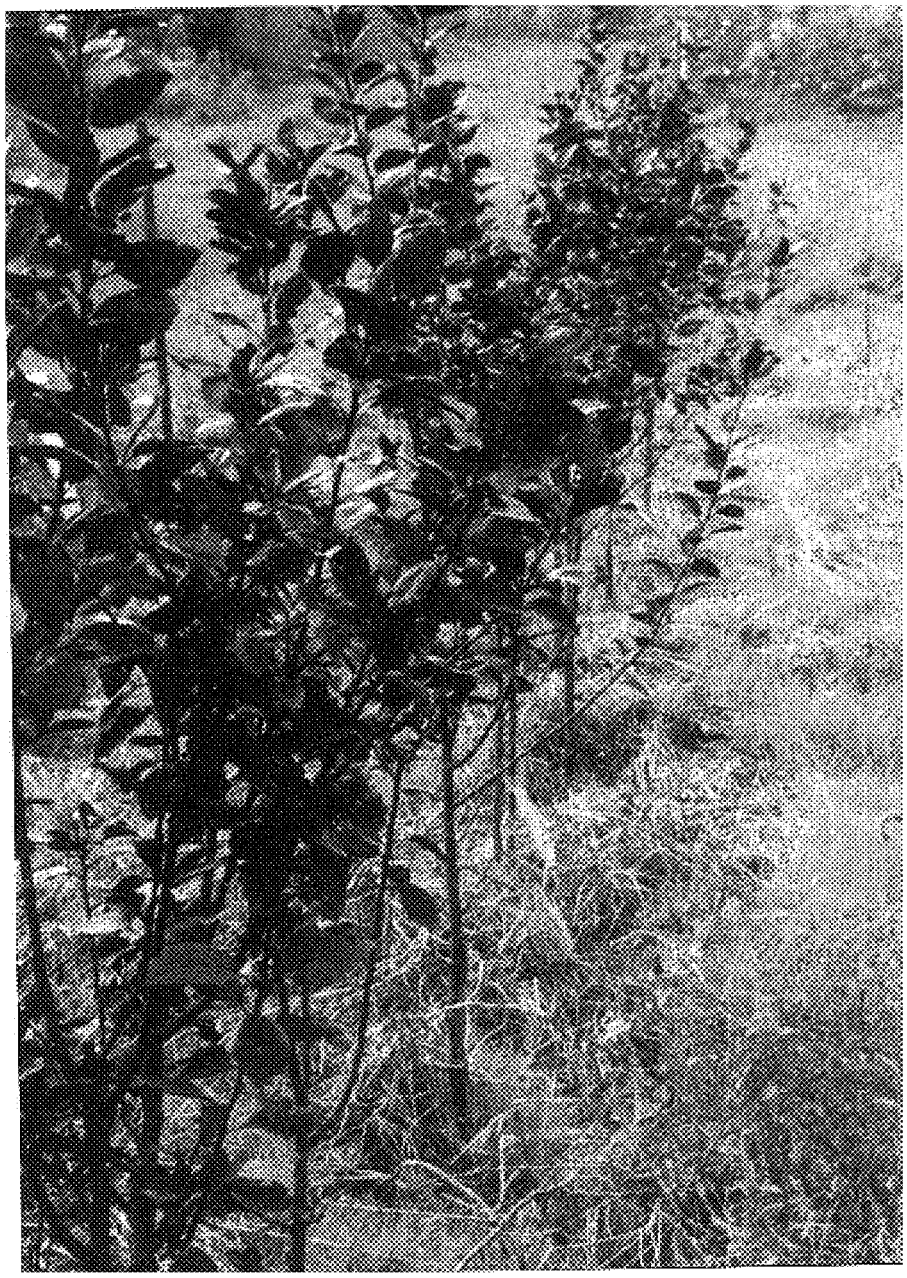
Figure 6:
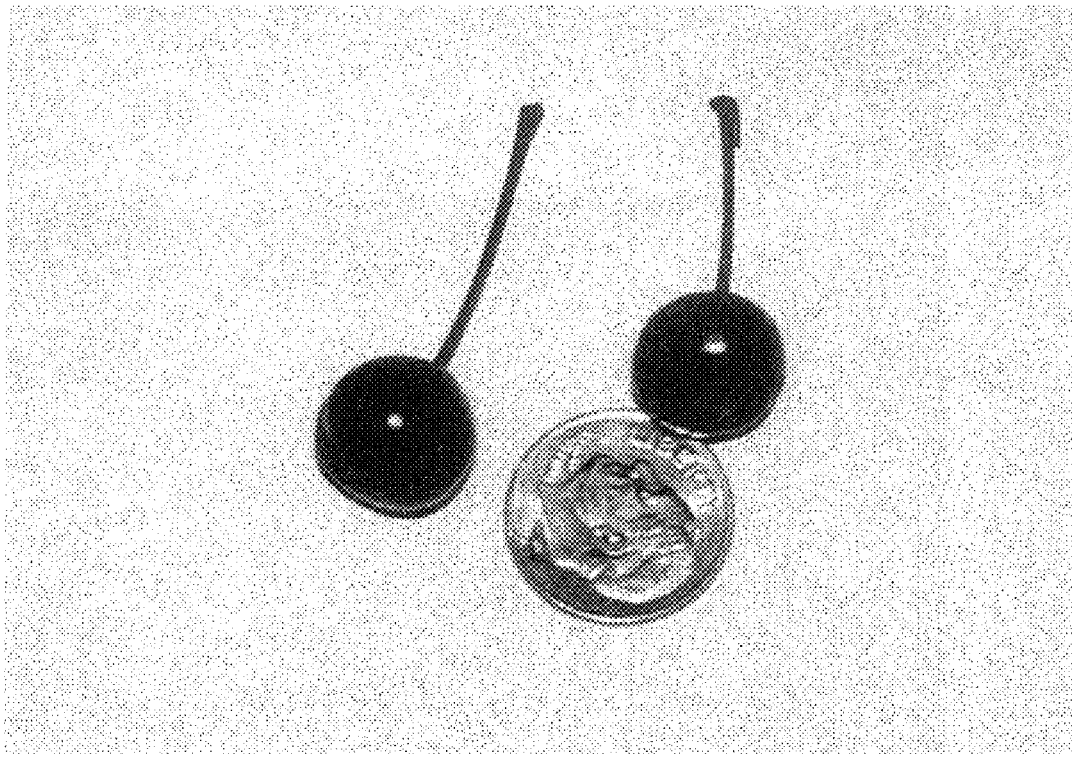
Figure 7:
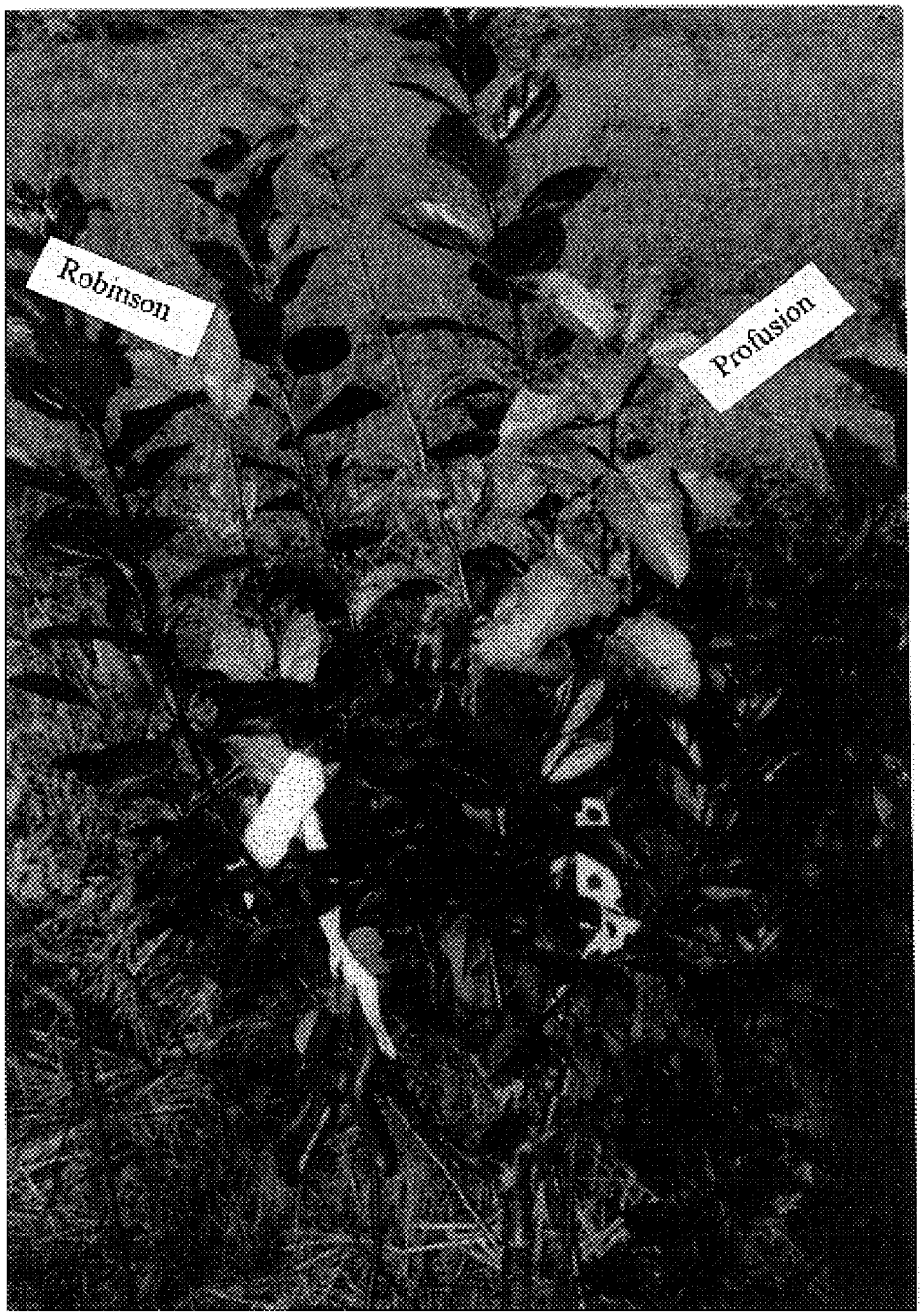
Figure 8:
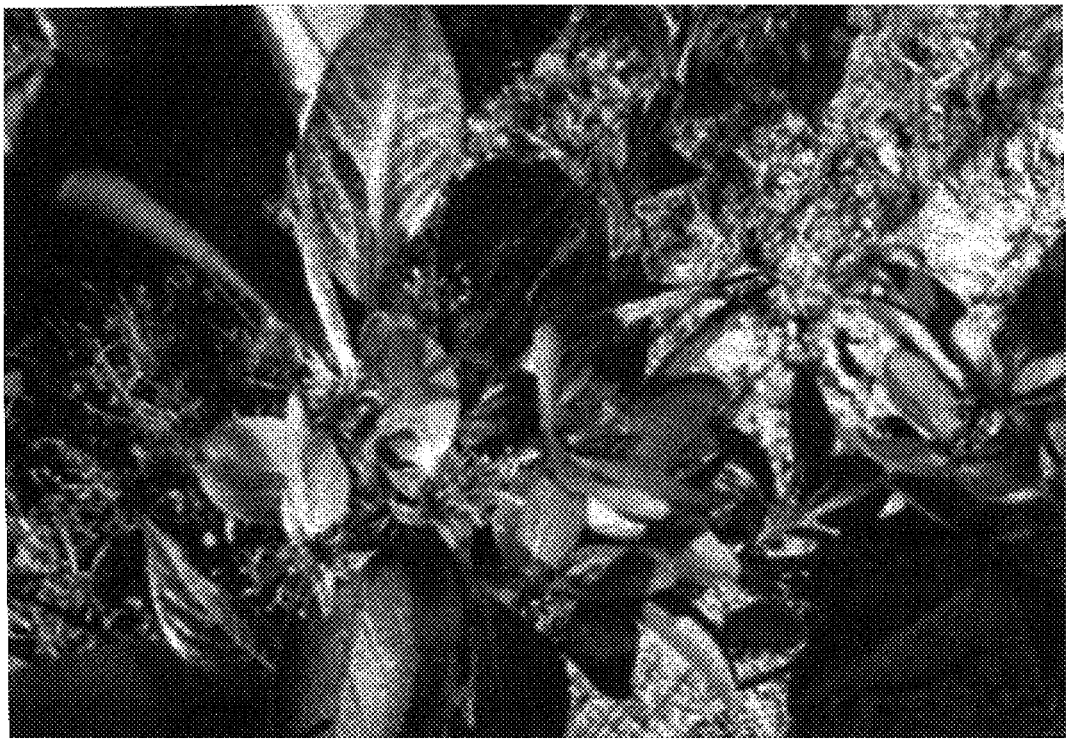

FIG. 1, 'Summer Wonder' 3 year plant;

FIG. 2, 'Summer Wonder' Spring foliage;

FIG. 3, 'Summer Wonder' Flowers and foliage;

FIG. 4, 'Summer Wonder' Flowers and foliage;

FIG. 5, 'Summer Wonder' Fall Foliage;

FIG. 6, 'Summer Wonder' Fruit;

FIG. 7, 'Summer Wonder' Comparison to summer foliage of other crabapple varieties;

FIG. 8, 'Summer Wonder' back of leaf.

PHOTOGRAPHS: (attached)

BOTANICAL DESCRIPTION OF THE PLANT

The original specimen of this 6 year old new *Malus* cultivar is now 8 feet (2.4 meters) tall and 5 feet (1.5 meters) wide with a trunk diameter of 3 inches (7.6 cm). Average growth is 2 feet (0.6 meters) per year. Mature leaf measurements range from 2.6 inches (6.6 cm) to 3.2 inches (7.6 cm) long to 1.5 inches (3.8 cm) to 1.7 (4.3 cm) wide. The mean leaf size is 2.9 inches (7.4 cm) long to 1.6 inches (4.0 cm) wide. The leaf is a typical shape of the species. Leaves are alternate, ovate, with acute bases and apices and serrate margins. Stems are dark purple with prominent lenticels which average 15 to 22 per stem section2.5 cm and 0.25 to 1.0 mm in diameter. The unique color of the leaves as measured by the Minolta Spectrophotometer (Model CM 2002)

| Name | L* | a* | b* | C* | h |
|---|---|---|---|---|---|
| Leaf Top | 27.8911 | 5.9290 | 3.2092 | 6.7418 | 28.4259 |
| Leaf Back | 33.1136 | 10.5724 | 4.7685 | 11.5980 | 24.2770 |
| Flower | 34.6821 | 26.2700 | 1.2371 | 26.2991 | 2.6962 |
| Stem Wood | 56.6625 | 3.7518 | 2.7246 | 4.6367 | 35.9872 |

Single flowers occur in March and bloom for 2 weeks. Buds are reddish purple in color and open to the characteristics pink/purple color designated by color ratings above. Individual flowers have 5 petals and average ½ inch (1.3 cm)×¼ inch (0.6 cm) wide and are arranged in clusters of 4 to 6 flowers per cluster. This contrasts with the typical small white flowers of the seedling 'Antonovka.' There is a strong pleasant fragrance. Fruit diameter averages 0.6 inches (1.6 cm). Fruit color is deep purple and listed in the table above. Bark has a typical color of the *M.* 'Antonovka' parent. Mature tree exhibits a spreading with branches extending from the trunk at typical angles ranging from 75 degrees to 35 degrees.

It is claimed:

1. A new and distinct cultivar of *Malus* tree named 'Summer Wonder', as herein described and illustrated.

* * * * *

'Summer Wonder'
3-year plant

'Summer Wonder'
*Spring foliage*

'Summer Wonder'
Flowers and foliage

'Summer Wonder'
Flowers and foliage

'Summer Wonder'
Fall Foliage

'Summer Wonder'
Fruit

'Summer Wonder'
Compared to Summer foliage (green larger leaf stalk) of M. 'Robinson' pictured on right and Summer foliage (green smaller leaf stalk) of M. Profusion pictured on left.

'Summer Wonder'
Back of leaf